(12) United States Patent
Benihoud et al.

(10) Patent No.: US 9,862,931 B2
(45) Date of Patent: Jan. 9, 2018

(54) ADENOVIRUS VACCINE VECTORS

(75) Inventors: Karim Benihoud, Paris (FR);
Anastasia Lanzi, Utrecht (NL); Michel Perricaudet, Ecrosnes (FR)

(73) Assignee: Institut Gustave Roussy, Villejuif (FR)

( * ) Notice: Subject to any disclaimer, the term of this patent is extended or adjusted under 35 U.S.C. 154(b) by 0 days.

(21) Appl. No.: 13/643,788

(22) PCT Filed: Apr. 28, 2011

(86) PCT No.: PCT/IB2011/051878
§ 371 (c)(1),
(2), (4) Date: Jan. 14, 2013

(87) PCT Pub. No.: WO2012/150478
PCT Pub. Date: Nov. 8, 2012

(65) Prior Publication Data
US 2013/0164327 A1 Jun. 27, 2013

(30) Foreign Application Priority Data

Apr. 28, 2010 (EP) .................................. 10290223
Jul. 13, 2010 (EP) .................................. 10290390

(51) Int. Cl.
| C12N 7/00 | (2006.01) |
| C07K 14/005 | (2006.01) |
| A61K 39/235 | (2006.01) |
| A61K 39/00 | (2006.01) |
| C12N 15/86 | (2006.01) |

(52) U.S. Cl.
CPC ............... *C12N 7/00* (2013.01); *A61K 39/00* (2013.01); *C07K 14/005* (2013.01); *C12N 15/86* (2013.01); *A61K 2039/5256* (2013.01); *A61K 2039/545* (2013.01); *A61K 2039/55* (2013.01); *C12N 2710/10322* (2013.01); *C12N 2710/10343* (2013.01); *C12N 2710/10362* (2013.01)

(58) Field of Classification Search
None
See application file for complete search history.

(56) References Cited

U.S. PATENT DOCUMENTS

| 6,127,525 | A * | 10/2000 | Crystal et al. | 530/388.22 |
| 6,153,435 | A * | 11/2000 | Crystal et al. | 435/455 |
| 2001/0026794 | A1* | 10/2001 | Kovesdi et al. | 424/93.21 |
| 2004/0038924 | A1* | 2/2004 | Davidson et al. | 514/44 |
| 2005/0048031 | A1* | 3/2005 | Haddada et al. | 424/93.2 |
| 2006/0281090 | A1* | 12/2006 | Lieber | C07K 14/005 435/6.16 |
| 2011/0130301 | A1* | 6/2011 | Havenga et al. | 506/9 |

FOREIGN PATENT DOCUMENTS

| EP | 1593742 A2 * 11/2005 | ............. C12N 15/86 |
| WO | WO 99/36545 * 7/1999 |

OTHER PUBLICATIONS

Lanzi A, Ben Youssef G, Perricaudet M, Benihoud K. Anti-adenovirus humoral responses influence on the efficacy of vaccines based on epitope display on adenovirus capsid. Vaccine. Feb. 4, 2011;29(7)1463-71. Epub Dec. 22, 2010.*
Okamba FR, Arella M, Music N, Jia JJ, Gottschalk M, Gagnon CA. Potential use of a recombinant replication-defective adenovirus vector carrying the C-terminal portion of the P97 adhesin protein as a vaccine against Mycoplasma hyopneumoniae in swine. Vaccine. Jul. 5, 2010;28(30):4802-9. Epub May 14, 2010.*
Xin KQ, Jounai N, Someya K, Honma K, Mizuguchi H, Naganawa S, et al. Prime-boost vaccination with plasmid DNA and a chimeric adenovirus type 5 vector with type 35 fiber induces protective immunity against HIV. Gene Ther 2005;12(Dec. 24):1769-77.*
Roberts DM, Nanda A, Havenga MJ, Abbink P, Lynch DM, Ewald BA, et al. Hexonchimaeric adenovirus serotype 5 vectors circumvent pre-existing anti-vector immunity. Nature 2006;441(May (7090)):239-43.*
McConnell MJ, Danthinne X, Imperiale MJ. Characterization of a permissive epitope insertion site in adenovirus hexon. J Virol 2006;80(Jun. 11): 5361-70.*
Singh N, Pandey A, Jayashankar L, Mittal SK. Bovine adenoviral vectorbased H5N1 influenza vaccine overcomes exceptionally high levels of pre-existing immunity against human adenovirus. Mol Ther 2008;16(May 5): 965-71.*
Vogels R, Zuijdgeest D, van Rijnsoever R, Hartkoorn E, Damen I, de Bethune MP, et al. Replication-deficient human adenovirus type 35 vectors for gene transfer and vaccination: efficient human cell infection and bypass of preexisting adenovirus immunity. J Virol 2003;77(Aug. 15):8263-71.*
Vellinga J, Van der Heijdt S, Hoeben RC. The adenovirus capsid: major progress in minor proteins. J Gen Virol. Jun. 2005;86(Pt 6):1581-8.*
Heemskerk B, Veltrop-Duits LA, van Vreeswijk T, ten Dam MM, Heidt S, Toes RE, van Tol MJ, Schilham MW. Extensive cross-reactivity of CD4+ adenovirus-specific Tcells: implications for immunotherapy and gene therapy. J Virol. Jun. 2003;77(11):6562-6.*
Seregin SS, Amalfitano A. Overcoming pre-existing adenovirus immunity by genetic engineering of adenovirus-based vectors. Expert Opin Biol Ther. Dec. 2009;9(12):1521-31.*
Zaiss AK, Machado HB, Herschman HR. The influence of innate and pre-existing immunity on adenovirus therapy. J Cell Biochem. Nov. 1, 2009;108(4):778-90.*
McConnell MJ, Hanna PC, Imperiale MJ. Adenovirus-based prime-boost immunization for rapid vaccination against anthrax. Mol Ther. Jan. 2007;15(1):203-10.*

(Continued)

*Primary Examiner* — Stacy B Chen
(74) *Attorney, Agent, or Firm* — Morgan, Lewis & Bockius LLP

(57) ABSTRACT

The invention relates to recombinant adenovirus displaying one or more heterologous epitope(s) on their fiber protein. These recombinant adenovirus are useful as vaccines for generating an immune response against said epitope(s) in individuals having a pre-existing anti-Ad immunity.

10 Claims, 9 Drawing Sheets

(56) References Cited

OTHER PUBLICATIONS

Figure 1:
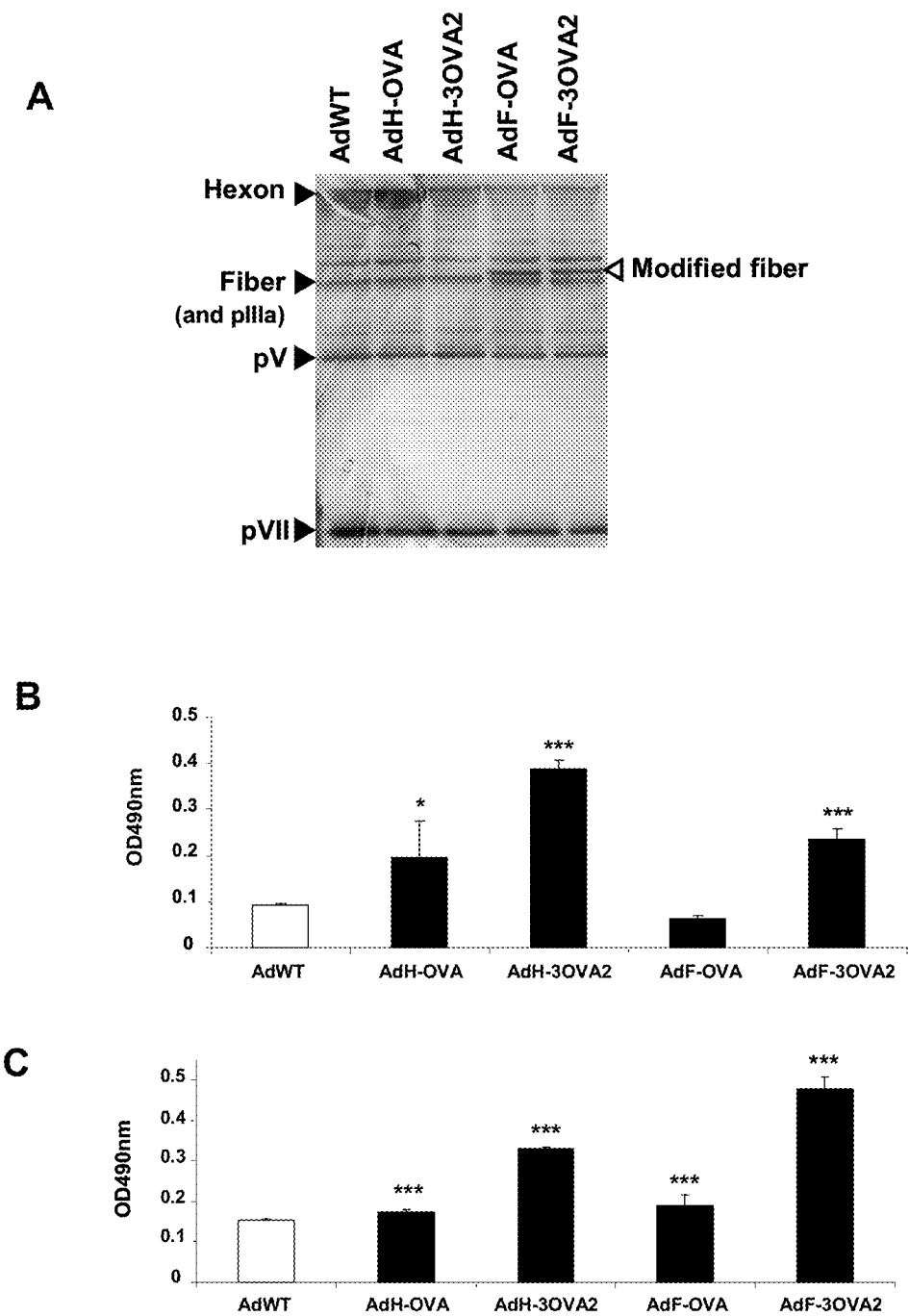

Krause A, Joh JH, Hackett NR, Roelvink PW, Bruder JT, Wickham TJ, Kovesdi I, Crystal RG, Worgall S. Epitopes expressed in different adenovirus capsid proteins induce different levels of epitope-specific immunity. J Virol. Jun. 2006;80(11):5523-30.*

Koizumi N, Mizuguchi H, Utoguchi N, Watanabe Y, Hayakawa T. Generation of fiber-modified adenovirus vectors containing heterologous peptides in both the HI loop and C terminus of the fiber knob. J Gene Med. Apr. 2003;5(4):267-76.*

Krasnykh V, Dmitriev I, Mikheeva G, Miller CR, Belousova N, Curiel DT. Characterization of an adenovirus vector containing a heterologous peptide epitope in the HI loop of the fiber knob. J Virol. Mar. 1998;72(3):1844-52.*

Reyes-Sandoval A, Sridhar S, Berthoud T, Moore AC, Harty JT, Gilbert SC, Gao G, Ertl HC, Wilson JC, Hill AV. Single-dose immunogenicity and protective efficacy of simian adenoviral vectors against Plasmodium berghei. Eur J Immunol. Mar. 2008;38(3):732-41. Erratum in: Eur J Immunol. May 2011;41(5):1501.*

Krause et al., Epitopes expressed in different adenovirus capsid proteins induce different levels of epitope-specific immunity, Journal of Virology, vol. 80, pp. 5523-5530, Jun. 2006.

Tatsis et al., Adenoviruses as vaccine vectors, Molecular Therapy, vol. 10, pp. 616-629, Oct. 2004.

Worgall et al., Protective immunity to pseudomonas aeruginosa induced with a capsid-modified adenovirus expressing P. aeruginosa OprF, Journal of Virology, vol. 81, pp. 13801-13808, Dec. 2007.

* cited by examiner

ADENOVIRUS VACCINE VECTORS

RELATED APPLICATIONS

The current application is a national stage entry of PCT/IB11/51878 filed on Apr. 28, 2011, which claims priority to European application EP 10290223.6 filed on Apr. 28, 2010 and European application EP 10290390.3 filed on Jul. 13, 2010.

SEQUENCE LISTING SUBMISSION VIA EFS-WEB

A computer readable text file, entitled "045636-5211_SequenceListing_10252012.txt," created on or about Oct. 23, 2012, with a file size of about 4 kb contains the sequence listing for this application and is hereby incorporated by reference in its entirety.

The invention relates to adenovirus-based vaccine vectors suitable in particular for administration to individuals presenting a preexisting anti-adenovirus immunity.

Adenovirus (Ad)-derived vectors have been largely used in preclinical and clinical studies targeting cancer or genetic diseases. Different studies have also investigated their use as vaccine platform against different antigens (TATSIS & ERTL, Mol Ther, 10, 616-29, 2004). Thus, recombinant Ad were shown to induce strong humoral and cellular responses against infectious pathogens such as Ebola (SULLIVAN et al., PLoS Med, 3, e177, 2006), HIV (SHU et al., Vaccine, 25, 1398-408, 2007), Hepatitis C virus (MARTIN et al., Vaccine, 26, 2471-81, 2008) but also against tumor-associated antigens (WARNIER et al., Int J Cancer, 67, 303-10, 1996). These vectors are relatively easy to construct and can be produced at high titer. In addition, they can transduce a large range of cells and trigger an innate immune response that helps in mounting immune responses to heterologous antigens (BENIHOUD et al., Gene Ther, 14, 533-44, 2007; DESCAMPS & BENIHOUD, Curr Gene Ther, 9, 115-27, 2009).

Most of the adenovirus-based vaccine vectors in humans are derived from adenovirus serotype 5 (Ad5). The preexistence of anti-Ad neutralizing antibodies directed against Ad5 in about 50 to 90% of humans (SUMIDA et al., J Immunol, 174, 7179-85, 2005) impairs gene transfer by these vectors which is a prerequisite for the expression of the antigen of interest.

Moreover, a strong anti-Ad cellular and humoral immunity is induced in non-immune receivers after the first administration that impairs the efficiency of subsequent Ad administrations (BENIHOUD et al., J Virol, 72, 9514-25, 1998; MCCOY et al., J Virol, 81, 6594-604, 2007). The use of prime-boost regimens based on a first delivery of plasmid followed by Ad injection (MCCONNELL et al., Mol Ther, 15, 203-10, 2007) constitutes one way to increase the potency of Ad vaccines but is still limited by anti-Ad humoral responses.

Several strategies have been developed to overcome anti-Ad humoral responses. Most of them capitalized on the best knowledge of capsid proteins structure allowing genetic modifications of Ad capsid components such as fiber and hexon proteins. A first approach is the development of Ad pseudotyped with a fiber from another serotype allowing the use of new prime-boost regimens (XIN et al., Gene Ther, 12, 1769-77, 2005). Second, replacement of hypervariable region (HVR) of hexon protein by the one from a serotype having low prevalence in humans, allowed Ad5 vector to escape from neutralizing antibodies (ROBERTS et al., Nature, 441, 239-43, 2006). Third, development of Ad vectors derived from non-Ad5 human serotypes (VOGELS et al., J Virol, 77, 8263-71, 2003; LEMCKERT et al., J Virol, 79, 9694-701, 2005) or even xenotypes broadened the set of vectors that can be used for vaccination (FARINA et al., J Virol, 75, 11603-13, 2001) (TATSIS et al., Gene Ther, 13, 421-9, 2006).

Since different regions of capsid proteins could accommodate peptides without affecting capsid assembly (KRASNYKH et al., Mol Ther, 1, 391-405, 2000), an alternative strategy was proposed to bypass the capacity of anti-Ad humoral response to block transgene expression. This approach does no longer require gene transfer for antigen expression but relies on epitope genetic insertion into Ad capsid. The efficacy of this approach was demonstrated by insertion of a neutralizing epitope from *P. aeruginosa* into hexon protein, resulting in a protective humoral response against pulmonary infection by this pathogen (WORGALL et al., J Clin Invest, 115, 1281-9, 2005; WORGALL et al., J Virol, 81, 13801-8, 2007). Insertion of an epitope from *B. anthracis* into Ad hexon protein was also shown to trigger a strong antibody response (MCCONNELL et al., J Virol, 80, 5361-70, 2006). One study has analyzed the influence of the site of insertion (hexon, penton base, fiber knob or protein IX) on epitope immunogenicity following one capsid-modified Ad administration. The best humoral response for an epitope of the hemagglutinin protein from influenza A virus was obtained following its insertion into fiber protein (KRAUSE et al., J Virol, 80, 5523-30, 2006). However, since the capsid-modified Ads were injected only once, the influence of the number of administrations in vaccination efficiency was not investigated.

In the present study, we seek to better characterize the influence of the number and the insertion site of the epitope on its immunogenicity following one or several administrations of capsid-modified Ad. For this purpose, $OVA_{323-339}$, an epitope derived from ovalbumin that contains a B cell epitope (BENZ et al., J Immunol, 151, 7206-13, 1993; FIFIS et al., Vaccine, 23, 258-66, 2004), was genetically inserted either into Ad hexon (AdH-3OVA2 and AdH-OVA) or fiber proteins (AdF-3OVA2 and AdF-OVA) of recombinant Ad.

After one intraperitoneal administration, all viruses triggered an efficient anti-ovalbumin response lasting more than 60 days, with AdH-3OVA2 being the most efficient. Comparable levels of anti-ovalbumin Abs were obtained with AdF-3OVA2 or a 10-fold lower dose of AdH-3OVA2, suggesting a direct role of the number of epitopes in the vaccination efficiency. In sharp contrast and surprinsingly, after two injections, anti-ovalbumin Ab responses were dramatically increased in mice injected with fiber-modified Ad compared to hexon-modified Ad. Passive transfer of serum from Ad-immune mice before challenge with Ad displaying OVA epitope into fiber or hexon protein helped to demonstrate a role of anti-Ad Abs in enhancement or reduction of anti-ovalbumin Ab production, respectively.

Our results showed that anti-epitope humoral response was not only influenced by the number of epitopes per capsid but also by pre-existing anti-Ad immunity, and underline that fiber protein constitutes a better site for epitope insertion in individuals presenting an anti-Ad immunity.

The invention thus provides a recombinant replication-defective adenovirus having one or more heterologous polypeptide(s) containing one or more target epitope(s) inserted into its fiber protein, for use as a vaccine generating an immune response against said target epitope(s) in a subject having a pre-existing humoral immunity against an adenovirus.

The recombinant replication-defective adenovirus of the invention can be obtained from different types of replication-defective adenovirus designed for human or animal therapy, which are known in themselves (for review, see for instance (DESCAMPS & BENIHOUD, Curr Gene Ther, 9, 115-27, 2009) by genetically inserting one or more heterologous polypeptide(s) containing the target epitope(s) into the fiber protein of said ademovirus. Preferably, it is derived from a replication-defective adenovirus of the same serotype as the adenovirus against which the subject receiving the vaccine has developed an humoral immunity. For instance, in the case of a human subject, the recombinant replication-defective adenovirus of the invention will be generally derived from Ad2 or Ad5, preferably from Ad5. The anti-adenovirus immunity may also result from a previous treatment with an adenovirus based vector; in this case, the recombinant replication-defective adenovirus of the invention will be derived from an adenovirus of the same serotype as said previously used vector.

The pre-existing humoral immunity to an adenovirus of a given serotype can be easily determined using methods well known in the art to detect the presence of antibodies directed against said serotype.

Advantageously, the recombinant replication-defective adenovirus of the invention can be used in a subject having previously received a recombinant replication-defective adenovirus of the same serotype, containing the same target epitope(s) inserted in a capsid protein other than the fiber protein, preferably in the hexon protein.

According to a preferred embodiment, said recombinant replication-defective adenovirus is used for repeated administrations (i.e at least two successive administrations) to a same subject. In this case it can also be used even in a subject having before the first administration, no anti-adenovirus humoral immunity against the serotype from which said replication-defective adenovirus is derived.

The invention also provides a replication-defective adenovirus having one or more heterologous polypeptide(s) containing one or more target epitope(s) inserted into its fiber protein and one or more heterologous polypeptide(s) containing the same target epitope(s) inserted into a capsid protein other than the fiber protein, preferably in the hexon protein. This adenovirus can be used advantageously for repeated administrations, in particular in subjects having no pre-existing anti-adenovirus humoral immunity against the serotype from which said replication-defective adenovirus is derived. The first administration allows to obtain a strong immune response against the target epitope(s) displayed on the capsid protein other than the fiber protein, while the subsequent administration(s) allow to further strengthen the immune response due to the display of the target epitope(s) on the fiber protein.

Methods for the genetic modification of Ad capsid proteins, as well as permissive sites, i.e. sites suitable for insertion of heterologous polypeptides in said proteins without affecting capsid assembly are also known in the art (see for instance KRASNYKH et al., 2000, cited above). In the case of fiber proteins, preferred insertion sites are generally located in the fiber knob, for instance added at the C-terminal end of the knob, or in the HI loop of the knob, as described for instance by BELOUSOVA et al., (J Virol, 76, 8621-31, 2002); in the case of hexon proteins, preferred insertion sites are generally located in the hypervariable loops, for instance in HRV5, or HRV2 (W U et al., J Virol, 79, 3382-90, 2005). The heterologous polypeptide(s) can be inserted inside the endogenous adenovirus sequence or in replacement of part of said sequence.

Optionally, the insertion of the heterologous polypeptide(s) can be combined with others modifications of the viral capsid proteins, for instance modifications having an influence on the viral tropism (and possibly reducing the viral toxicity). By way of non-limitative examples of such modifications one can mention: the pseudotyping with the fiber protein of an adenovirus of another serotype, the deletion of the motif RGD of the penton base which is responsible of the interaction with integrins, the modification of the amino-acid residues of the fiber protein involved in the interaction with the CAR receptor or with heparan sulfates. A particularly preferred modification is the deletion of the HVR5 loop of the hexon protein, as disclosed in PCT WO 2007/148148; if need be, said loop can be replaced by an heterologous polypeptide containing one or more target epitope(s), as described above.

A "heterologous polypeptide" herein refers to a polypeptide having a sequence other than the sequence of an adenoviral fiber protein or a fragment thereof. Preferably, said heterologous polypeptide is at least 5, more preferably at least 8, and still more preferably at least 10 amino-acids long; it can be up to 200, preferably up to 100, more preferably up to 50, and advantageously up to 25 amino-acids long. Optionally, two or more heterologous polypeptides can be inserted in the fiber protein at two or more different permissive sites, for instance at the C-terminal end and in the HI loop of the knob. In the same way, two or more heterologous polypeptides can be inserted in the hexon protein at two or more different permissive sites, for instance in the HRV5, and HRV2 loops. In these cases, the global size of the inserts within the fiber or the hexon protein should remain preferably less than 100 amino-acids long. Each heterologous polypeptide may comprise one or more target epitopes against which one wishes to raise an immune response. The epitopes can be derived from a same antigen or from different antigens.

The antigen can be for instance an antigen from an infectious agent (including bacteria, viruses, fungi, and protozoa) or a tumour antigen. The target epitope can be a B or a T-cell epitope, preferably a B-cell epitope.

The invention further provides methods for generating an immune response against one or more target epitope(s) in a subject.

According to a first embodiment, the invention provides a method for generating an immune response against one or more target epitope(s) in a subject having a pre-existing humoral immunity against an adenovirus, wherein said method comprises administering to said subject a recombinant replication-defective adenovirus having one or more heterologous polypeptide(s) containing said target epitope(s) inserted into its fiber protein.

According to a second embodiment, the invention provides a method for generating an immune response against one or more target epitope(s) in a subject having or not a pre-existing humoral immunity against an adenovirus, wherein said method comprises:

a) administering to said subject a recombinant replication-defective adenovirus having one or more heterologous polypeptide(s) containing said target epitope(s) inserted into its fiber protein;

b) re-administering said recombinant replication-defective adenovirus at least once to said subject.

Due to the fact that the first administration of the recombinant replication-defective adenovirus induces anti-adenoviral immunity this second embodiment can, if wished, be used in a subject having no pre-existing humoral immunity against an adenovirus before said first administration.

According to a third embodiment, the invention provides a method for generating an immune response against one or more target epitope(s) in a subject having or not a pre-existing humoral immunity against an adenovirus, wherein said method comprises:

a) administering to said subject a first recombinant replication-defective adenovirus having one or more heterologous polypeptide(s) containing said target epitope(s) inserted into a capsid protein other than the fiber protein, preferably in the hexon protein;

b) administering to said subject a recombinant replication-defective adenovirus of the same serotype as the first one, having one or more heterologous polypeptide(s) containing the same target epitope(s) inserted into its fiber protein;

c) optionally, re-administering said recombinant replication-defective adenovirus at least once to said subject.

According to a fourth embodiment, the invention provides a method for generating an immune response against one or more target epitope(s) in a subject having or not a pre-existing humoral immunity against an adenovirus, wherein said method comprises:

a) administering to said subject a first replication-defective adenovirus having one or more heterologous polypeptide(s) containing one or more target epitope(s) inserted into its fiber protein and one or more heterologous polypeptide(s) containing the same target epitope(s) inserted into a capsid protein other than the fiber protein, preferably in the hexon protein;

b) administering to said subject a recombinant replication-defective adenovirus of the same serotype as the first one, selected among:

i) the same recombinant replication-defective adenovirus as the one used for the first administration;

ii) a recombinant replication-defective adenovirus having one or more heterologous polypeptide(s) containing the same target epitope(s) inserted into its fiber protein; and no target epitope inserted into another capsid protein than the fiber protein.

c) optionally, re-administering said recombinant replication-defective adenovirus at least once to said subject.

The methods according to the third and fourth embodiments can advantageously be used in subjects having no pre-existing humoral immunity against an adenovirus. In this case the first administration allows both to obtain a strong immune response against the target epitope(s) displayed on the capsid protein other than the fiber protein, and to induce anti-adenoviral immunity while the subsequent administration(s) allow to further strengthen the immune response due to the display of the target epitope(s) on the fiber protein.

Advantageously, the methods of the invention comprise a previous step of determining in the subject to be treated, the presence or the absence of antibodies against adenovirus of the serotype of the recombinant replication-defective adenovirus to be used.

Routes, dosage, and frequency of the recombinant replication-defective adenovirus of the invention will be chosen depending on the subject, of the disease to treat or prevent through generation of the immune response, and of the serotype of the adenovirus which are administered. Generally, they will be administered by injection (e.g., intracutaneous, intramuscular, intravenous, intraperitoneal or subcutaneous), however, other routes of administration can be used, such as oral, intranasal, vaginal or rectal delivery. Typically, and by way of way of non-limitative examples, the quantity of viral particles for each administration may vary from about $10^7$ to $10^{10}$ particles, and the number of administrations may vary from 2 to 6, two consecutive administration being generally separated by an interval of about 15 days to 2 months.

FIGURE LEGENDS

FIG. 1 Epitope detection on capsid-modified Ad. (A) Silver staining of capsid-modified Ad. $10^{10}$ vp (viral particles) of either a control Ad (AdWT) or a capsid-modified Ad (AdH-3OVA2, AdH-OVA, AdF-3OVA2, AdF-OVA) were separated on a 10% polyacrylamide gel. Major capsid components are identified (black arrow) and the difference between modified or native fiber is indicated (white arrow). (B and C) Detection of OVA- and 3OVA2-epitopes on virions. ELISA plates were coated with 100 ng of native (B) or denaturated (C) viruses and incubated with a rabbit polyclonal antibody against the ovalbumin protein. The binding was detected with HRP-conjugated secondary antibody. One of two experiments is shown, n=6; means+SD of sixtuplates.

Figure 2:
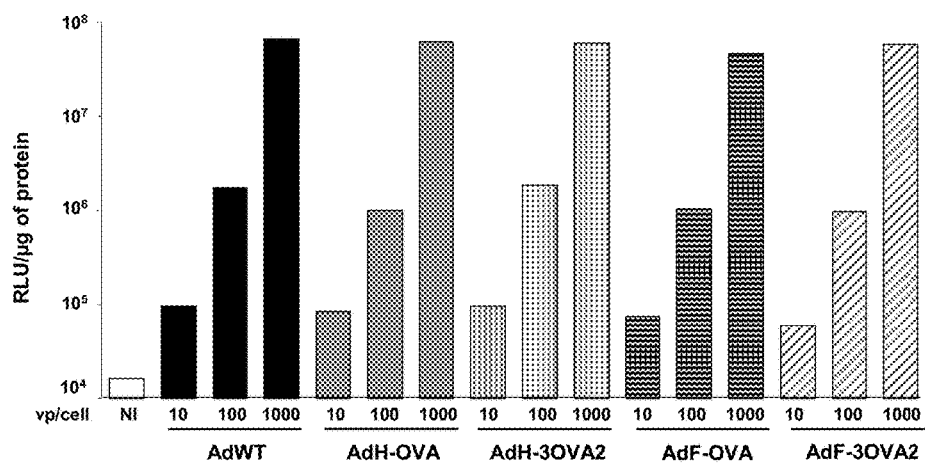

FIG. 2 In vitro gene transfer by capsid-modified Ad. CHO-CAR were mock-infected (PBS) or infected with increasing MOI of lacZ recombinant AdWT, AdH-OVA, AdH-3OVA2, AdF-OVA and AdF-3OVA2. β-Gal activity, expressed as RLU/μg of protein, was measured in cell lysates 24 h later. Experiments run in duplicate were performed twice and representative results are shown.

Figure 3:
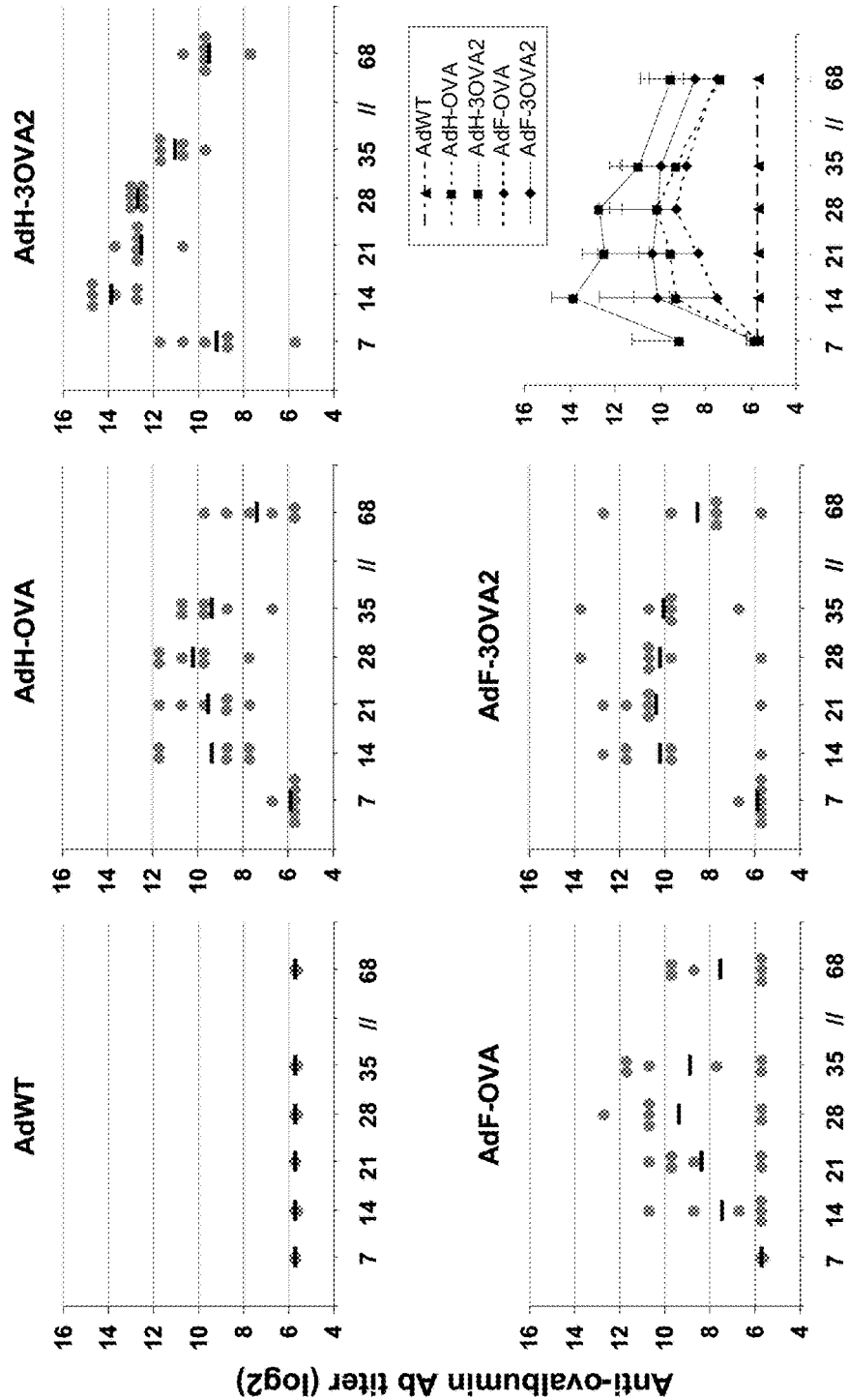

FIG. 3 Kinetic of anti-ovalbumin humoral response. C57Bl/6 mice were immunized intra-peritoneally with $10^{10}$ vp of a control Ad (AdWT) or one capsid-modified Ad (AdH-3OVA2, AdH-OVA, AdF-3OVA2 or AdF-OVA). Anti-ovalbumin IgG titers were determined by ELISA at different days p.i. (post-injection). Ab titers below 100 were plotted as 50. One of two experiments is shown, circles and bars represent results of individual mice (n=6) and means, respectively.

Figure 4:
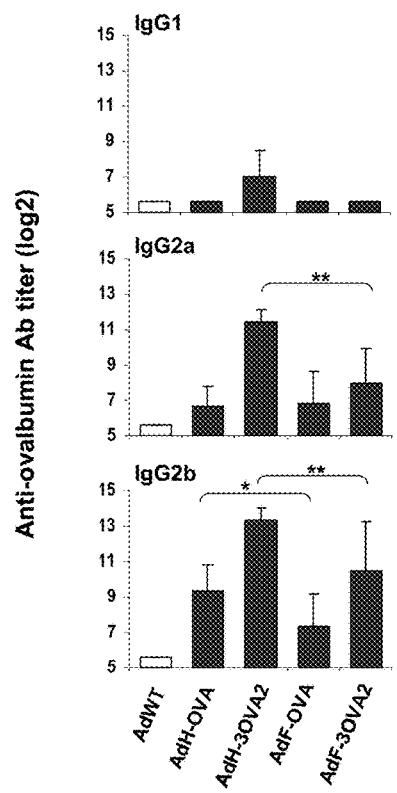

FIG. 4 Characterization of anti-ovalbumin Abs isotypes. C57Bl/6 mice were immunized intra-peritoneally with $10^{10}$ vp of a control Ad (AdWT) or one capsid-modified Ad (AdH-3OVA2, AdH-OVA, AdF-3OVA2 or AdF-OVA). Anti-ovalbumin IgG1, IgG2a and IgG2b titers were determined by ELISA at day 21 p.i. Ab titers below 100 were plotted as 50. One of two experiments is shown, n=6; means+SD.

Figure 5:
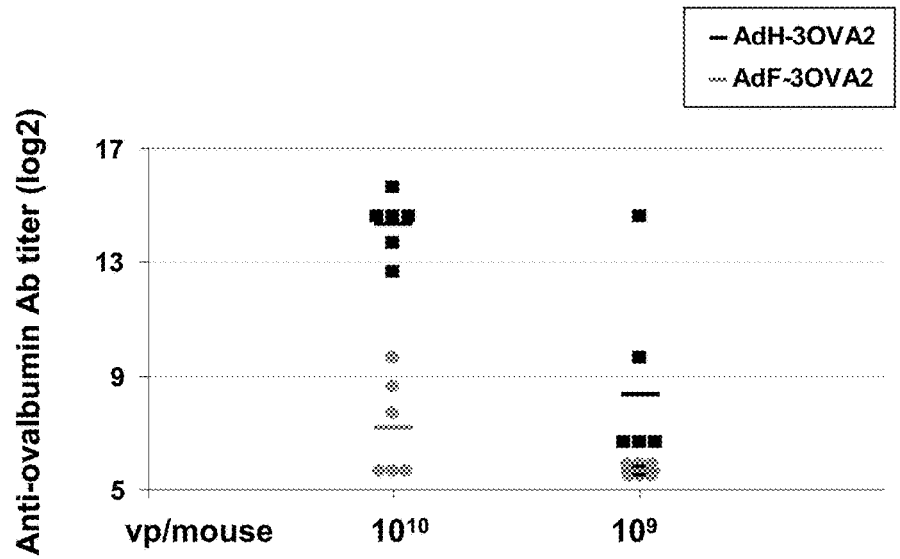

FIG. 5 Dose-dependence of anti-ovalbumin humoral response. C57Bl/6 mice were immunized intra-peritoneally with $10^9$ or $10^{10}$ vp of AdH-3OVA2 or AdF-3OVA2. Anti-ovalbumin IgG titers were determined by ELISA at day 14 p.i. One of two experiments is shown, circles and bars represent results of individual mice (n=6) and means, respectively.

Figure 6:
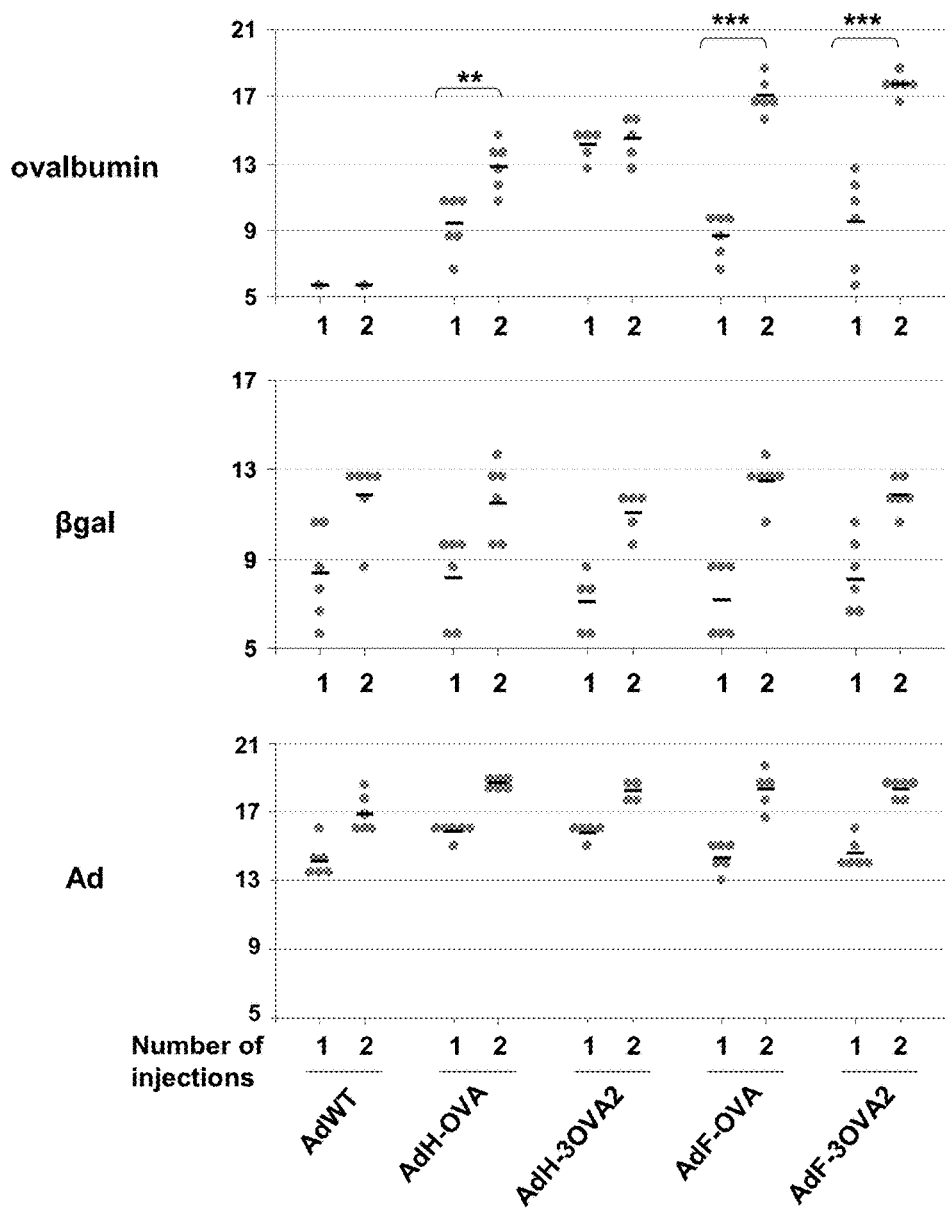

FIG. 6 Repeated administration of capsid-modified Ad. C57Bl/6 mice were immunized twice two weeks apart intra-peritoneally with $10^{10}$ vp of AdWT or capsid-modified Ad and sera were collected at day 14 p.i. Anti-ovalbumin, anti-βgal and anti-Ad IgG titers were determined by ELISA at day 14 p.i. Ab titers below 100 were plotted as 50. One of two experiments is shown, circles and bars represent results of individual mice (n=6) and means, respectively.

Figure 7:
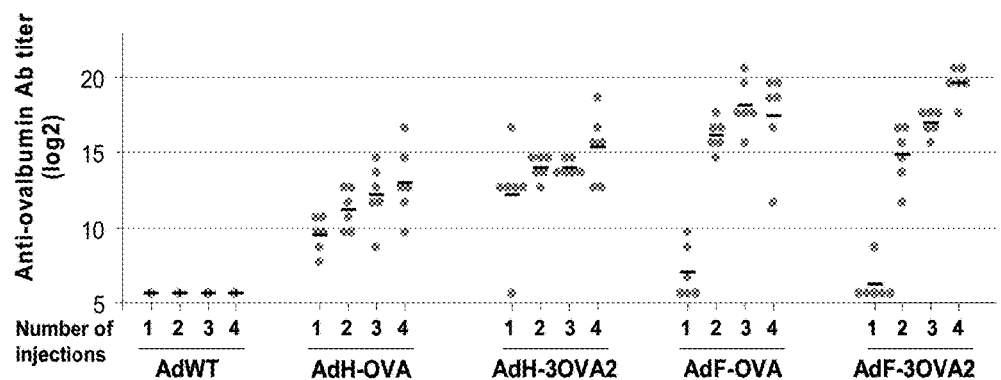

FIG. 7 Anti-ovalbumin responses after several virus administrations. C57Bl/6 mice were injected four times at two week intervals intraperitoneally with $10^{10}$ vp of AdWT or capsid-modified Ad and sera were collected at day 14 after each injection. Ab titers below 100 were plotted as 50. One of two experiments is shown, circles and bars represent results of individual mice (n=6) and means, respectively.

Figure 8:
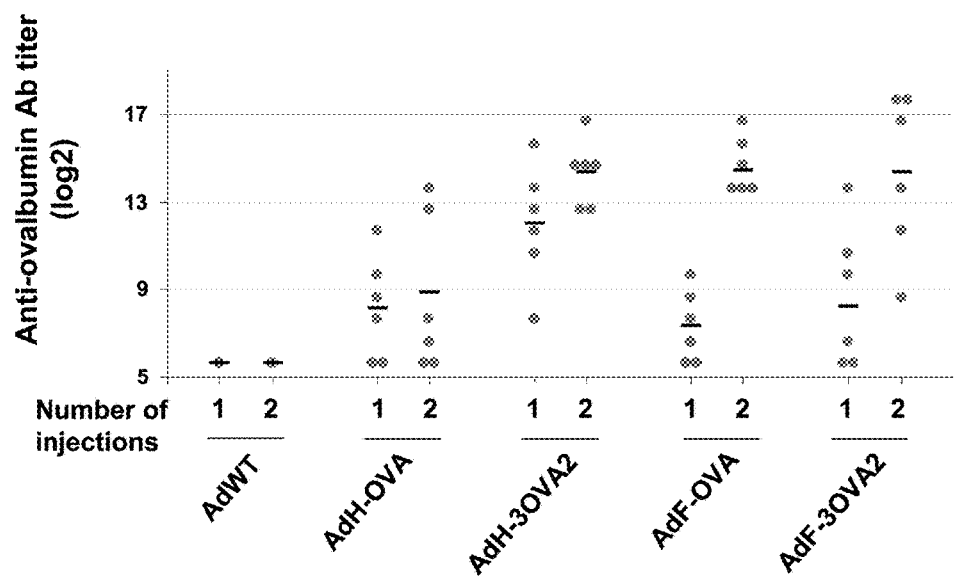

FIG. 8 Anti-ovalbumin responses after subcutaneous administration of capsid-modified Ad. C57Bl/6 mice were injected subcutaneously twice two weeks apart with $10^{10}$ vp of AdWT or capsid-modified Ad and sera were collected at day 14 p.i. Ab titers below 100 were plotted as 50. One of two experiments is shown, circles and bars represent results of individual mice (n=6) and means, respectively.

Figure 9:
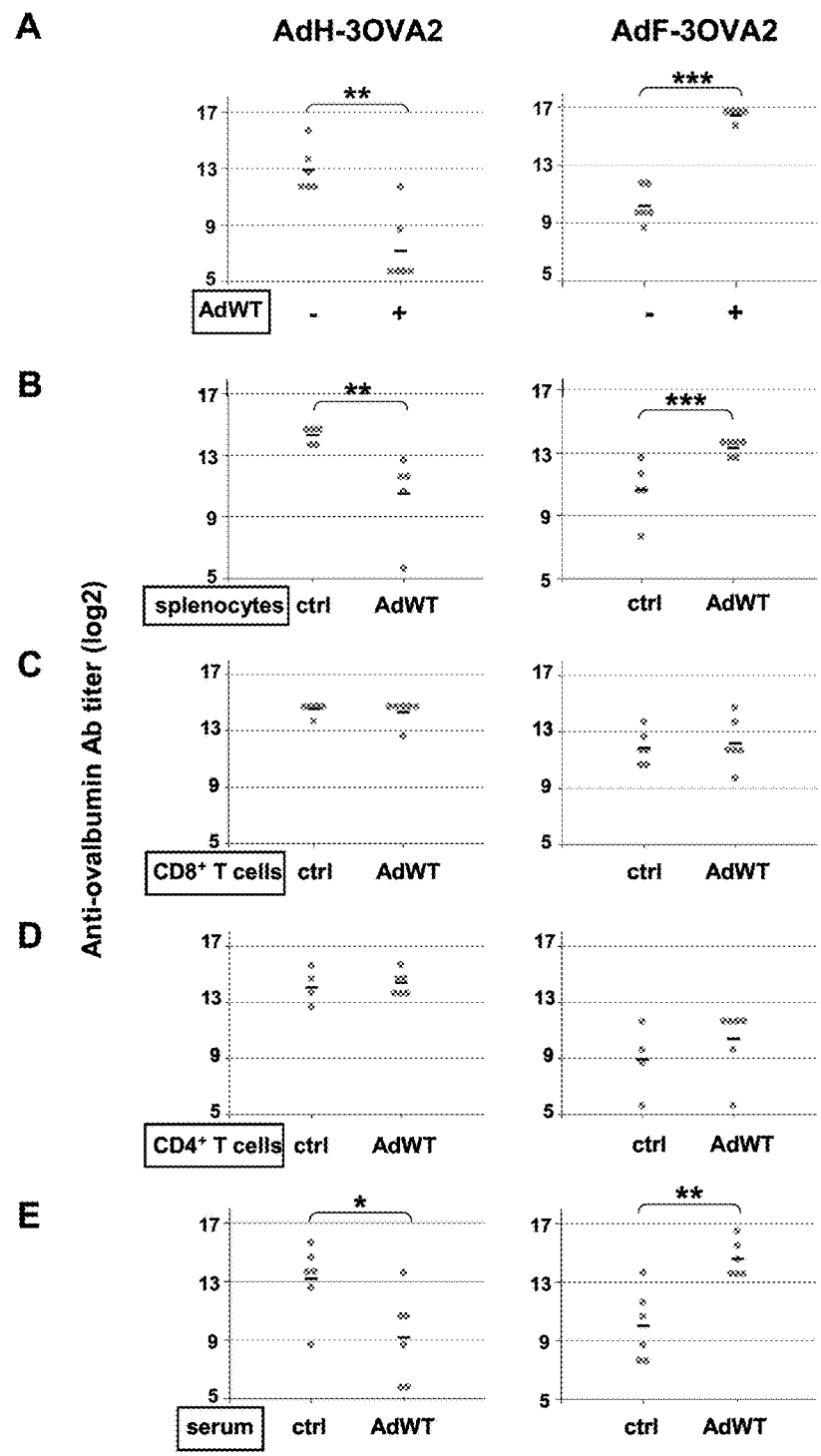

FIG. 9 Influence of anti-Ad immunity on the anti-ovalbumin humoral response. (A) C57Bl/6 mice injected with AdWT or mock-injected were injected two weeks later with AdH-3OVA2 or AdF-3OVA2 ($10^{10}$ vp). Anti-ovalbumin IgG titers were determined by ELISA at day 14 p.i. Ab titers below 100 were plotted as 50. One of two experiments is shown, circles and bars represent results of individual mice (n=6) and means, respectively. Splenocytes (B), CD4$^+$ (C), CD8$^+$ (D) lymphocytes or serum (E) from mock-injected mice or from mice injected with AdWT were adoptively transferred into naive mice before intraperitoneal injection of AdH-3OVA2 or AdF-3OVA2 ($10^{10}$ vp). Anti-ovalbumin IgG titers were determined by ELISA at day 14 p.i. Ab titers below 100 were plotted as 50. Circles and bars represent results of individual mice (n=6) and means, respectively.

Figure 10:
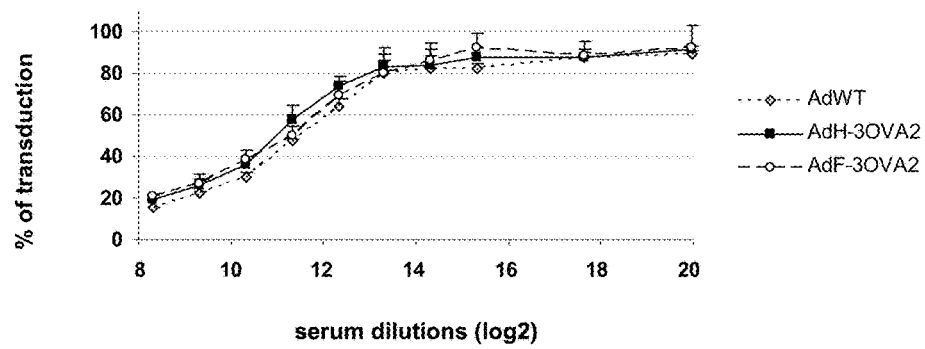

FIG. 10 Neutralization of capsid-modified Ad by anti-Ad Abs. AdWT or capsid-modified viruses (AdH-3OVA2 or AdF-3OVA2) were mixed with serial dilutions of anti-Ad serum and then incubated with 293A cells. βgal activity was measured one day later and expressed as percentage of transduction relative to cells infected with virus alone.

Figure 11:
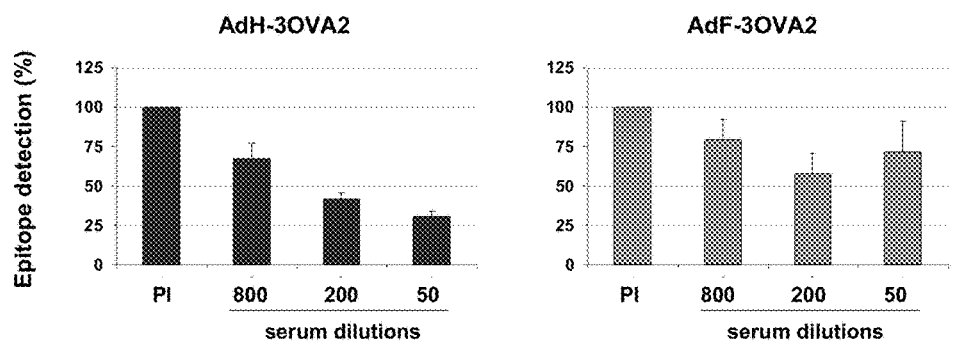

FIG. 11 Masking of 3OVA2 epitope by anti-Ad Abs. AdWT, AdH-3OVA2 or AdF-3OVA2 coated on 96-well plates were incubated with serum from naive or Ad-immune mice and 3OVA2 epitope accessibility was assessed using anti-ovalbumin Abs. 3OVA2 epitope detection on virions in different conditions of incubation was expressed relative to detection of 3OVA2 on virus incubated with control serum. One of two experiments is shown, histograms represent means±SD (n=10).

Figure 12:
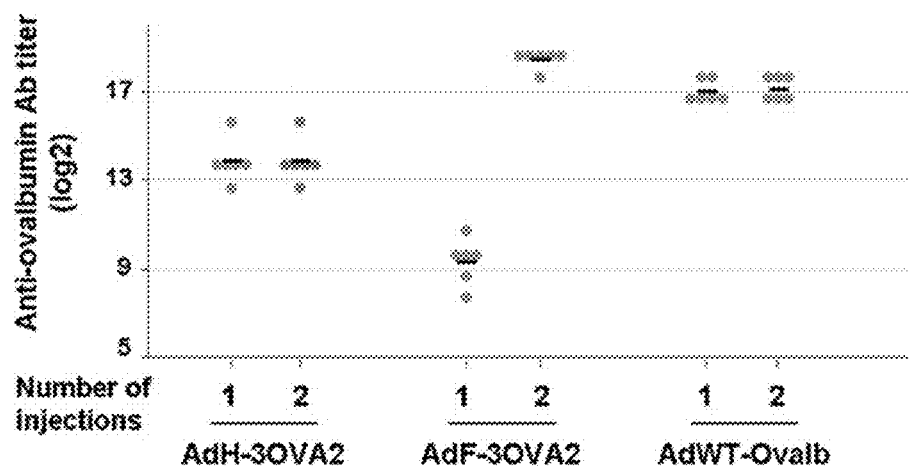

FIG. 12. Comparison of capsid-modified Ad to a recombinant Ad expressing ovalbumin as a transgene. C57BL/6 mice were immunized twice two weeks apart intra-peritoneally with $10^{10}$ vp of capsid-modified Ad (AdH-3OVA2 or AdF-3OVA2) or AdWT-Ovalb, expressing ovalbumin as a transgene. Sera were collected at day 14 p.i. and anti-ovalbumin IgG titers were determined by ELISA. Ab titers below 100 were plotted as 50. One of two experiments is shown, circles and bars represent results of individual mice (n=6) and means, respectively.

Figure 13:
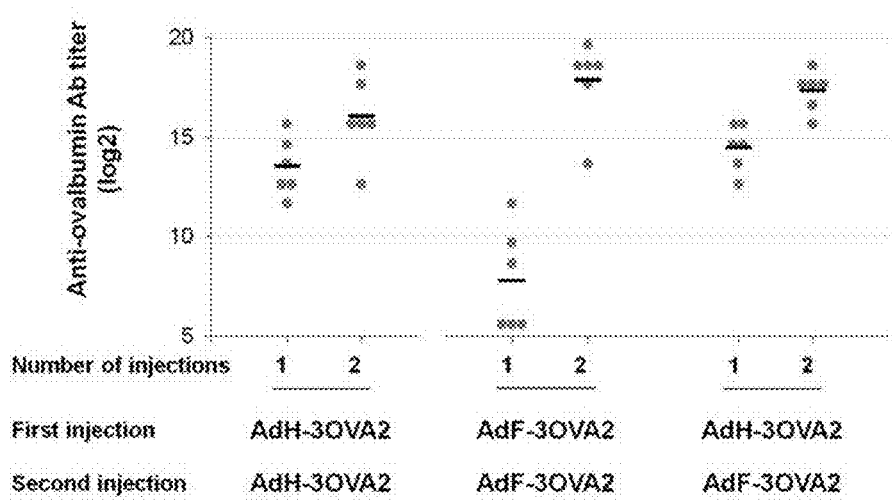

FIG. 13. Anti-ovalbumin responses after priming and boosting with different capsid-modified Ad. C57BL/6 mice were immunised twice two weeks a part intra-peritoneally with $10^{10}$ vp of capsid-modified Ad (AdH-3OVA2 or AdF-3OVA2) or were immunised first with AdH-3OVA2 and second with AdF-3OVA2. Sera were collected at day 14 p.i. and anti-ovalbumin IgG titers were determined by ELISA. Ab titers below 100 were plotted as 50. One of two experiments is shown, circles and bars represent results of individual mice (n=6) and means, respectively.

MATERIALS AND METHODS

Adenoviral Vectors

LacZ-recombinant control AdWT (AE18 in ref. (VIGNE et al., J Virol, 73, 5156-61, 1999)) was derived from Ad5 with E1 and E3 regions deleted. AdH-OVA and AdH-3OVA2, derived from AdWT, contain respectively a short (OVA$_{323\text{-}339}$: ISQAVHAAHAEINEAGR (SEQ ID NO: 1), referred in the text as OVA peptide) or a long (OVA$_{320\text{-}342}$: SLKISQAVHAAHAEINEAGREV (SEQ ID NO: 2), referred in the text as 3OVA2 peptide) peptide derived from ovalbumin. These peptides were inserted into the hexon protein in place of $_{269}$TTEAAAGNGDNLT$_{281}$ (SEQ ID NO: 3) of hypervariable region 5. AdF-OVA and AdF-3OVA2 contain respectively OVA or 3OVA2 peptide inserted in place of T$_{539}$QETGDTTPS$_{548}$ (SEQ ID NO: 4) into the HI loop of the fiber protein. All modified viruses (Table 1) were constructed using recombinational cloning in *E. coli* (CROUZET et al., Proc Natl Acad Sci USA, 94, 1414-9, 1997).

TABLE 1

| Virus | Modified protein | Adaptor | Inserted peptide (SEQ ID NO: #) | Adaptor | Titer ($\times 10^{12}$ vp/ml) |
|---|---|---|---|---|---|
| AdWT | — | — | — | — | 7.5 ± 0.6 |
| AdH-OVA | hexon | G | ISQAVHAAHAEINEAGR (1) | LGG | 5.9 |
| AdH-3OVA2 | hexon | G | SLKISQAVHAAHAEINEAGREV (2) | LGG | 7.9 ± 1.4 |
| AdF-OVA | fiber | SS | ISQAVHAAHAEINEAGR (1) | GSS | 9.5 |
| AdF-3OVA2 | fiber | SS | SLKISQAVHAAHAEINEAGREV (2) | GSS | 8.1 ± 0.4 |

All viruses were obtained using standard procedures as described (MARTIN et al., Mol Ther, 8, 485-94, 2003), stored at −80° C. in PBS-7% glycerol and titrated by spectrophotometry (1 OD$_{260}$=1.1×10$^{12}$ viral particle (vp)/ml).

Oligonucleotides

Oligonucleotides used for insertion and PCR detection of nucleotide sequences encoding 3OVA2 and OVA epitopes are described in Table 2.

TABLE 2

| Name | Nucleotide sequence (SEQ ID NO: #) | Target |
|---|---|---|
| Hex | 5'- atgggatgaagctgctactg -3' (5) | Hexon |
| IM21A | 5'-ggcatatctcaagctgtccatgcagcacatgcagaaatcaatgaagcaggcagacttggcggccc- 3' (6) | OVA into hexon |

TABLE 2-continued

| Name | Nucleotide sequence (SEQ ID NO: #) | Target |
|---|---|---|
| IM21B5'- | ttagggccgccaagtctgcctgcttcattgatttctgcatgtgctgcatggacagcttgagatatgcc-3' (7) | OVA into hexon |
| IM22A5'- | ggcagcctgaagatatctcaagctgtccatgcagcacatgcagaaatcaatgaagcaggcagagaggtgcttggcggccc-3' (8) | 3OVA2 into hexon |
| IM22B5'- | ttagggccgccaagcacctctctgcctgcttcattgatttctgcatgtgctgcatggacagcttgagatatcttcaggctgcc- 3' (9) | 3OVA2 into hexon |
| HigU15'- | cagctccatctcctaactgtagactaaatg -3' (10) | Fiber |
| IM23A5'- | gtaaccctaaccattacactaaacggttctagcatatctcaagctgtccatgcagcacatgcagaaatcaatgaagcaggagc-3' (11) | OVA into fiber |
| IM23B5'- | gctagaacctctgcctgcttcattgatttctgcatgtgctgcatggacagcttgagatatgctagaaccgtttagtgtaatggttagg-3' (12) | OVA into fiber |
| IM24A5'- | gtaaccctaaccattacactaaacggttctagcagcctgaagatatctcaagctgtccatgcagcacatgcagaaatcaatgaagcaggcagagaggtgggttctagc-3' (13) | 3OVA2 into fiber |
| IM24B5'- | gctagaacccacctctctgcctgcttcattgatttctgcatgtgctgcatggacagcttgagatatcttcaggctgctagaaccgtttagtgtaatggttagg-3' (14) | 3OVA2 into fiber |

PCR Detection of Epitope Coding Sequences

Adenoviral DNA was extracted from purified AdWT and capsid-modified viruses and DNA concentrations were determined by OD260. The primers used in PCR reactions (Table 2) are as follows: Hex and IM21B for AdH-OVA, Hex and IM22B for AdH-3OVA2, HigU1 and IM23B for AdF-OVA, HigU1 and IM24B for AdF-3OVA2. The amplification mixture contained 200 µM dNTPs, 0.5 µM of each primer, 1.5 U of Taq Polymerase (Biolabs, Ipswich, Mass.), 1×TaqPol buffer, and 150 ng of total DNA. The reaction was initiated by a 4 min denaturation step at 94° C. Amplification occurred during 30 cycles, each cycle consisting of 1 min at 94° C., 1 min at 53° C., and 2 min at 72° C. PCR products were analyzed by gel electrophoresis.

SDS-PAGE and Silver Stain Analysis

Purified viruses ($10^{10}$ vp) were resuspended in Laemmli lysis buffer, boiled for 5 min and loaded onto a 10% NuPage gel (Novex, Invitrogen, CA). After electrophoresis, the gel was stained with a silver staining kit (Invitrogen, Carlsbad, Calif.).

Detection of OVA- and 3OVA2-Epitopes on Virions

To assess whether the epitopes were present or accessible on the capsid surface, denaturated or native viruses were coated on 96-well plates (Nunc, Roskilde, Denmark). Viruses were inactivated at 56° C. during 30 minutes and 0.1% SDS was added. Spectrophotometric reading was performed at 215 and 225 nm to determine virus concentrations and 100 ng were coated on 96-well plates. Alternatively, same quantities of native viruses were coated. After overnight incubation at 4° C., non-specific sites were blocked with 5% milk PBS-Tween, then plates were washed and incubated with a rabbit polyclonal antibody against the ovalbumin protein (AB1225, Millipore, Mass.) for 1 hour. After washing, an anti-rabbit IgG peroxydase-linked Ab (NA934, Amersham Biosciences, Saclay, France) was added for 1 hour and peroxidase activity was revealed by incubation with the substrate o-Phenylenediamine dihydrochloride (Sigma-Aldrich, Lyon, France) for 30 min. The reaction was stopped by addition of 3N HCl and spectrophotometric reading was performed at 490 nm.

The masking of ovalbumin-derived epitopes by anti-Ad Abs was investigated as follows. Viruses ($10^9$ vp) were coated on 96-well plates (Nunc) and dilutions of serum from mice injected twice with AdWT were added. Sera from pre-immune mice were used as controls. Following a one hour incubation, plates were washed, and incubated with a rabbit polyclonal anti-ovalbumin Ab (AB1225) overnight at 4° C. The binding of anti-ovalbumin Ab was revealed as described above.

Cells 293A were maintained as recommended by Invitrogen. CHO-CAR, kindly provided by Dr Bergelson, were described previously (BERGELSON et al., Science, 275, 1320-3, 1997).

CHO-CAR Transduction

All the experiments were performed in 12-well dishes (Corning Glass Works, Corning, N.Y.) and run in duplicate. Confluent cell monolayers of CHO-CAR cells were infected with increasing MOI (10, $10^2$ and $10^3$ vp/cell) of AdWT or capsid-modified viruses in 400 µl of serum-free medium. One hour later, 2 ml of complete medium were added. After 24 h, cells were lysed and β-galactosidase (β-gal) activity was measured using a chemiluminescent assay (BD Biosciences Clontech, Palo Alto, Calif.). Protein content was determined using the Bio-Rad Protein Assay (Bio-Rad Laboratories, Hercules, Marnes-la-Coquette, France). Results are expressed as relative light units (RLU) per µg of protein.

Mice 7-week-old C57BL/6 female mice were purchased from Janvier (Le Gesnest Saint Isle, France) or Harlan (Gannat, France). They were conditioned at least for one week in the animal facilities before beginning of the experiments. All animal experiments were approved by the IGR Institutional Animal Care and Use Committee.

In Vivo Experiments

Control or capsid-modified viruses ($10^9$ or $10^{10}$ vp) in PBS (200 μL) were injected intra-peritoneally. Repeated injections were performed at intervals of 2 weeks (total injection between 2 and 4). Blood samples were collected before virus injection and at different intervals thereafter. Mice sera were prepared and analyzed for the presence of anti-ovalbumin, anti-βgalactosidase (βgal) and anti-Ad antibodies by ELISA as described below.

Serum and Cell Transfer Experiments

For sera and splenocytes transfer experiments, mice were injected intra-peritoneally twice two weeks apart with AdWT ($10^{10}$ vp in 200 μL of PBS) or PBS (200 μL). At day 15 after the second injection, mice were sacrificed and spleens were removed. Spleens were crushed in RPMI medium supplemented with 5% SVF, 1% non essentials amino acids, 1% glutamine, 1% pyruvate and $5 \times 10^{-5}$ M β-mercaptoethanol, and filtered through a 100 μm cell strainer. After removal of blood cells by ACK Lysing Buffer (Invitrogen, Cergy-Pontoise, France), the cells were resuspended and the concentration was adjusted at $5 \cdot 10^7$ cells/mL. In parallel, sera were prepared from blood. Serum (diluted to the third in PBS) or splenocytes ($10^7$ splenocytes in 200 μL of RPMI medium) were injected intravenously into mice retro-orbital plexus. The following day, mice were injected intra-peritoneally with either AdH-3OVA2 or AdF-3OVA2 ($10^{10}$ vp). Blood were collected at day 15 after Ad injection. Mice sera were prepared and analyzed for the presence of anti-ovalbumin, anti-βgal and anti-Ad antibodies by ELISA as described below.

For CD4$^+$ and CD8$^+$ T cells transfer experiments, splenocytes were prepared as described above and resuspended in 1 mL of complemented RPMI medium. Then, PE-Cy7 anti-CD3 (eBioscience, CA, USA), APC anti-CD19 (eBioscience) and APC anti-NK-1.1 (BD Bioscience) Abs were added during 30 minutes at 4° C. After washing, cells were resuspended, filtered through a 40 μm cell stainer and 7-AAD (BD Bioscience) was added. CD3$^+$ cells were sorted on a DakoCytomation MoFlo cytometer (Beckman Coulter, Villepinte, France) and collected. After centrifugation, cells were resuspended in 1 mL of complemented RPMI medium and incubated with PE anti-CD4 and FITC anti-CD8 Abs (BD Bioscience) during 30 minutes at 4° C. After cells sorting, two fractions corresponding to CD4$^+$CD3$^+$ and CD8$^+$CD3$^+$ T cells were obtained. CD4$^+$ ($2 \cdot 10^6$) or CD8$^+$ ($10^6$) T cells in 200 μL of RPMI medium were injected intravenously into mice retro-orbital plexus. The following day, mice were injected intra-peritoneally either with AdH-3OVA2 or with AdF-3OVA2 ($10^{10}$ vp/mouse). Blood were collected at day 15 after Ad injection, Determination of Specific Antibodies Ovalbumin-specific antibodies in the sera were determined by ELISA. After coating of 96-well plates (Nunc) with 1 μg of ovalbumin protein (Calbiochem, Merck chemicals, Nottingham, England), serial dilutions of the sera in 5% milk PBS-Tween were added. Bound antibody was detected with peroxidase-conjugated anti-mouse IgG, IgG1, IgG2a or IgG2b isotypes goat antibodies (Southern Biotechnology Associates, Birmingham, Ala.). The peroxidase was revealed by incubation with the substrate o-Phenylenediamine dihydrochloride (Sigma-Aldrich) for 30 min. The reaction was stopped by addition of 3N HCl and spectrophotometric reading was performed at 490 nm. βgal- and Ad-specific antibodies in the sera were determined by ELISA as described previously (BENIHOUD et al., Gene Ther, 14, 533-44, 2007). Titers were calculated as reciprocal dilutions 2-fold above background values.

Anti-Adenoviral Neutralizing Antibody Assay

LacZ-recombinant wild-type or capsid-modified viruses were mixed with serial dilutions of serum samples from pre-immune or Ad-immune mice decomplemented for 30 min at 56° C. Then, after a one-hour incubation at 37° C., the mixture was incubated with 293A cells (40,000 cells/well, multiplicity of infection of 50) in 96-well plates for 1 h at 37° C. Then, 100 μl of complete medium was added, and the cells were cultured for 19 h. Cells were washed and incubated with 100 μl of lysis buffer (6 mM Na2HPO4, 10 mM KCl, 0.1 mM MgSO4, 50 mM 2-mercaptoethanol, and 0.5% Triton X-100) containing 0.1 mg of βgal substrate (4-methyl-umbelliferylb-D-galactoside; Sigma) for 30 min at 37° C. After excitation at 360 nm, the resulting fluorescence was measured at 460 nm with a Wallach Victor 2 (Perkin-Elmer, Waltham, Mass.). For each serum dilution, the percentage of transduction was calculated as follows: (experimental value−background value [without virus])/(positive control [without serum]−background value)×100.

Statistical Analyses

A Mann-Whitney test, recommended for groups fewer than 30 mice, was conducted. Differences were considered significant when $P<0.05$.

Results

Production and Characterization of Ad Displaying Ovalbumin-Derived Epitopes

In order to analyze whether the site of epitope insertion may influence vaccination efficacy of Ad displaying epitopes on their capsid, ovalbumin-derived epitopes (OVA and 3OVA2) were genetically inserted into either hexon (AdH-OVA and AdH-3OVA2) or fiber (AdF-OVA and AdF-3OVA2) proteins of a lacZ recombinant Ad. All capsid-modified Ad were produced and purified at titers comparable to AdWT presenting a wild-type capsid (Table 1). SDS-PAGE analyses confirmed no differences in virus composition and integrity between capsid-modified Ad and AdWT (FIG. 1A). In addition, there was no difference in the ability of capsid-modified Ad to tranduce CHO-CAR cells, a cell line overexpressing Ad primary receptor (FIG. 2).

The presence of OVA or 3OVA2 epitope coding sequence in Ad genome was confirmed by PCR performed on purified virions (data not shown). For AdF-OVA and AdF-3OVA2, the presence of the epitope within the fiber was demonstrated by a modification of the fiber migration pattern in SDS-Page (FIG. 1A). Using a polyclonal anti-ovalbumin antibody, OVA or 3OVA2 epitope were detected by ELISA performed on native (FIG. 1B) or denatured (FIG. 1C) purified virions. 3OVA2 epitope was detected on native or denatured AdH-3OVA2 and AdF-3OVA2. OVA epitope was detected on either native or denatured AdH-OVA but only on native AdF-OVA (FIG. 1B).

Anti-Ovalbumin Humoral Responses Triggered by One Injection of Capsid-Modified Adenovirus To assess the ability of capsid-modified Ad to mount an anti-ovalbumin humoral response, C57Bl/6 mice were injected intra-peritoneally with AdWT or capsid-modified Ad ($10^{10}$ viral particle (vp)). Sera were collected until 68 days post-injection (p.i.) and anti-ovalbumin IgG Ab titers were measured. Most of mice injected with capsid-modified Ad displayed anti-ovalbumin Abs whereas AdWT-injected mice did not. Production of Abs was detected as soon as day 7 p.i., peaked between day 14 and day 28 p.i. and was still detectable 68 days p.i. for all capsid-modified Ad (FIG. 3). Interestingly, at all time points, anti-ovalbumin Ab titers were higher when the epitope (OVA or 3OVA2) was inserted into hexon rather than into fiber protein. Thus, AdH-3OVA2-injected mice displayed much higher anti-ovalbumin Ab titers than AdF-3OVA2-injected mice at all time points (p<0.05 for all the kinetic, and notably, p<0.01 at day 14 and 28). Anti-ovalbumin titers were also stronger at day 14 p.i. in sera of AdH-OVA-injected mice than AdF-OVA (FIG. 3, p<0.05). Careful analysis of IgG subisotypes revealed a high production level of IgG2a and IgG2b anti-ovalbumin Abs, reminiscent of the Th1 bias of anti-Ad humoral responses (BENIHOUD et al., J Virol, 72, 9514-25, 1998). Interestingly, AdH-3OVA2-injected mice displayed significantly higher titers of anti-ovalbumin IgG2a and IgG2b subisotypes compared to AdF-3OVA-2-injected mice (FIG. 4, p<0.01).

To better compare the efficiency of vaccination by hexon- or fiber-modified Ad, mice were injected with the two viruses giving the best humoral responses (AdH-3OVA2 or AdF-3OVA2) at the dose of $10^{10}$ or $10^9$ vp and anti-ovalbumin antibodies were measured at day 14 p.i. Anti-ovalbumin antibody levels increase with viral dose for both AdH-3OVA2 and AdF-3OVA2, however whatever the dose examined they were higher in AdH-3OVA2-injected mice than in AdF-3OVA2 (FIG. 5). Anti-ovalbumin titers were comparable in mice treated with $10^9$ vp of AdH-3OVA2 and in mice treated with $10^{10}$ vp of AdF-3OVA2, thus underlining a 10-fold better efficacy of AdH-3OVA2 compared to AdF-3OVA2 (FIG. 5).

Altogether, these results pointed out that following one capsid-modified Ad injection, a better humoral response is obtained when the epitope is inserted into hexon protein.

Anti-Ad Pre-Existing Immunity Shapes Anti-Ovalbumin Humoral Responses Induced by Capsid-Modified Ad To determine to what extent anti-ovalbumin humoral responses could be boosted, C57BL/6 mice were injected intra-peritoneally at days 0 and 14 with AdWT or different capsid-modified Ad. Sera were collected at day 14 after the first and the second injection. Compared to mice receiving one virus administration, anti-ovalbumin Ab titers present an 11- and 1.5-fold increase in mice injected twice with AdH-OVA and AdH-3OVA2, respectively (FIG. 6). In sharp contrast, after the second injection, AdF-OVA and AdF-3OVA2-injected mice exhibit a 314- and 110-fold increase in anti-ovalbumin Ab titer, respectively, compared to the ones observed after the first viral administration (FIG. 6). This better efficacy of fiber-modified Ads was still observed following 4 intraperitoneal virus injections (FIG. 7) and remarkably was also found using another mode (subcutaneous) of virus administration (FIG. 8). It should be emphasized that such a dramatic increase in humoral responses after the second injection of fiber-modified Ad was only observed for anti-ovalbumin Abs. Indeed, anti-βgal and anti-Ad Abs were not differentially increased after challenge with fiber-modified Ad compared to hexon-modified Ads or AdWT (FIG. 6).

Our results stress that after the second virus administration, a most powerful humoral response is obtained with epitope insertion into fiber protein, thus reversing the hierarchy observed after one virus injection (FIGS. 3 to 5). Since we ruled out a difference in the kinetic of anti-ovalbumin Ab responses between hexon and fiber-modified Ad (FIG. 3), we examined a potential role of anti-Ad immunity in controlling anti-ovalbumin Abs levels. Mice were either injected with PBS or with AdWT ($10^{10}$ vp), and then two weeks later, mice received either AdH-3OVA2 or AdF-3OVA2 injection. Mice injected with AdWT followed by AdH-3OVA2 displayed a 21-fold decrease in serum anti-ovalbumin Ab titers compared to mice injected with PBS followed by AdH-3OVA2 (FIG. 9A), thus suggesting that pre-existing Ad immunity dampens the capacity of the immune system to mount a humoral response against ovalbumin epitope inserted into hexon protein. In contrast, mice injected successively with AdWT and AdF-3OVA2 displayed a 55-fold increase in serum Ab titers compared to mice injected with PBS and AdF-3OVA2 (FIG. 9A).

Anti-Ad Humoral but not Cellular Responses Potentiate Anti-Ovalbumin Humoral Responses Induced by Fiber-Modified Ad To examine how the immune response to Ad influences on anti-ovalbumin humoral responses, we studied the respective roles of anti-Ad lymphocytes and antibodies. First, we analysed anti-ovalbumin humoral responses in mice adoptively transferred with naïve or anti-Ad splenocytes before administration of capsid-modified Ad. FIG. 9B indicated that compared to their naïve counterparts, splenocytes from Ad-immune mice dramatically reduced anti-ovalbumin response in mice injected with AdH-3OVA2 but potentiated this response in AdF-3OVA2-injected mice (FIG. 9B). To further define the role of anti-Ad cellular immunity, CD4$^+$ or CD8$^+$ T lymphocytes from mice injected with PBS or AdWT were sorted and adoptively transferred into naïve recipients before administration of AdH-3OVA2 or AdF-3OVA2. FIG. 9D and FIG. 9E ruled out a major influence of anti-Ad CD4$^+$ or CD8$^+$ lymphocytes in mounting anti-ovalbumin Ab responses. In sharp contrast, transfer of serum from Ad-immune mice into naive mice before administration of AdH-3OVA2 or AdF-3OVA2 led either to a strong inhibition or to a dramatic increase in anti-ovalbumin Ab responses, respectively.

Altogether, these results underline that humoral anti-Ad pre-existing immunity strongly shapes the humoral response against an ovalbumin-derived epitope inserted into Ad capsid. Most importantly, our data underline that, in Ad immune mice, fiber constitutes the best site of peptide insertion to mount an efficient anti-epitope humoral response.

Masking of Ovalbumin-Derived Epitope Inserted into Hexon Protein by Anti-Ad Antibodies In order to understand how anti-Ad Abs affect anti-ovalbumin humoral responses, we first examined whether there was a difference in sensitivity of AdH-3OVA2 or AdF-3OVA2 to antibodies raised against AdWT. First, AdH-3OVA2, AdF-3OVA2 and AdWT were incubated without or with different anti-Ad serum dilutions, then, their ability to transduce CAR-expressing cells was analysed. The results indicated for all viruses a comparable inhibition of cell transduction by anti-Ad antibodies as documented by measurement of βgal activity (FIG. 10). Thus, the difference in mounting anti-ovalbumin Ab responses between hexon-modified and fiber-modified Ads was not linked to a differential neutralization by anti-Ad antibodies.

As an alternative hypothesis, we postulated that anti-Ad Abs could induce a steric hindrance and inhibit in vivo the recognition of ovalbumin epitope by B cells, leading to a decrease of anti-ovalbumin humoral responses in AdH-3OVA2-injected mice. This hypothesis is supported by previous reports showing that hexon protein was the main target of anti-Ad antibodies (ROBERTS et al., Nature, 441, 239-43, 2006). To get insight into ovalbumin epitope accessibility, capsid-modified Ad were immobilized on ELISA plates and incubated with serum from naive or AdWT-injected mice, then, 3OVA2 epitope was detected by an anti-ovalbumin polyclonal Ab. FIG. 11 showed an anti-Ad-Ab-mediated inhibition of 3OVA2 epitope detection on both AdH-3OVA2 and AdF-3OVA2. However, it should be emphasized that detection of ovalbumin epitope was strongly reduced at high serum concentration for AdH-3OVA2 compared to AdF-3OVA2, thus suggesting that anti-Ad Abs reduced accessibility of the epitope when inserted into hexon protein.

Vaccine Efficiency of Hexon Modified or Fiber-Modified Ads Compared to Recombinant Ad Expressing the Antigen of Interest.

To compare the vaccine efficiency of the epitope display strategy to the classical approach based on Ad driving the expression of the antigen of interest, C57BL/6 mice were injected two times either with capsid-modified Ad (AdH-3OVA2 or AdF-3OVA2) or with AdWT-Ovalb, bearing an expression cassette for ovalbumin protein. After the first injection, anti-ovalbumin Ab titers obtained were higher for mice injected with AdWT-Ovalb compared to AdH-3OVA2 or AdF-3OVA2. However, after the second virus administration, a comparable anti-ovalbumin humoral response was obtained in AdF-3OVA2 and AdWT-Ovalb-injected mice (FIG. 12), thus underlying the potency of the epitope display strategy of vaccination after two virus injections.

Vaccine Efficiency after Priming with Hexon-Modified Ad and Boosting with Either Hexon-Modified or Fiber-Modified Ad.

We analysed the anti-ovalbumin humoral response induced by a first administration of AdH-3OVA2 followed by a second administration of AdF-3OVA2, to compare it with those induced by two consecutive administrations of either AdH-3OVA2 or AdF-3OVA2. FIG. 13 shows that mice injected with AdH-3OVA2 followed by AdF-3OVA2 present after the second administration a level of anti-ovalbumin Ab response comparable to mice injected two times with AdF-3OVA2, and superior to mice injected two times with AdH-3OVA2.

Discussion

Our results indicated that after one Ad injection, the strongest anti-ovalbumin humoral responses were triggered when the epitope was inserted into hexon protein, thus underlining an important role of epitope number (240×3 for hexon-modified Ad versus 12×3 for fiber-modified Ads). In sharp contrast, after two or more injections, a remarkable increase in anti-ovalbumin humoral responses was obtained when the epitope was inserted into fiber protein. In addition, our data unravelled a role of anti-Ad immunity in controlling anti-epitope humoral responses.

To study the influence of the insertion site on epitope immunogenicity, $OVA_{323-339}$ alone (OVA) or surrounded by residues flanking this epitope in ovalbumin protein (3OVA2) was inserted into hexon or fiber protein. In vitro studies showed that this epitope was better recognized by polyclonal anti-ovalbumin Abs on AdH-3OVA2 and AdF-3OVA2 rather than on AdH-OVA and AdF-OVA. This suggests that $OVA_{323-339}$ accessibility or conformation is improved by addition of flanking residues. After virion denaturation, $OVA_{323-339}$ epitope was better detected on AdH-3OVA2 versus AdF-3OVA2 and on AdH-OVA versus AdF-OVA in strict correlation with the number of epitopes per capsid. However, the results were strikingly different for native virions. Indeed, $OVA_{323-339}$ is better detected on AdF-3OVA2 than AdH-3OVA2, thus suggesting that fiber protein naturally protruding from the virion is a more suitable site for display of a B cell epitope.

After one injection of capsid-modified Ad into C57Bl/6 mice, a higher anti-ovalbumin humoral response was obtained with AdH-OVA and AdH-3OVA2 compared to AdF-OVA and AdF-3OVA2. This hierarchy between hexon and fiber modified-Ads is maintained throughout the kinetic up to 68 days p.i. Moreover, a dose of $10^9$ vp of AdH-3OVA2 led to similar levels of anti-ovalbumin Abs than $10^{10}$ vp of AdF-3OVA2, demonstrating a 10-fold better efficacy of vaccination by AdH-3OVA2. These results were surprising given the better $OVA_{323-339}$ accessibility into fiber protein. However, they could be linked to the number of epitopes per capsid (240×3 versus 12×3) and suggest a direct role of epitope number on the vaccination efficiency.

Following the second injection, a boost of anti-ovalbumin Abs was observed in all mice groups. However, whereas hexon-modified Ads led only to a modest increase in anti-ovalbumin Ab responses, fiber-modified Ads triggered a dramatic increase. As a consequence, the second injection of capsid-modified Ads reverses the hierarchy observed after one injection, with fiber-modified Ads triggering the highest anti-ovalbumin Ab responses. Interestingly, this bias is maintained even after up to 4 injections. The boosting efficacy of anti-ovalbumin humoral responses by fiber-modified Ads was observed not only after intraperitoneal but also after subcutaneous Ad injection and thus was not dependent on the mode of virion administration. Remarkably, this boosting efficacy appears to be specific of the epitope inserted into the capsid since no difference in the degree of boosting of anti-βgal or anti-Ad Abs was observed between all viruses. To the best of our knowledge, this is the first report showing a difference in vaccination efficiency among capsid-modified Ads upon reinjection.

The dramatic increase in anti-ovalbumin Ab responses observed after the second injection of fiber-modified Ads could not be explained by different kinetic compared to hexon-modified Ads. Therefore, we hypothesized a role of Ad immunity in shaping anti-epitope Ab responses. In fact, Ad-immune mice injected with AdF-3OVA2 displayed much higher anti-ovalbumin Ab levels than naive mice injected with AdF-3OVA2. To identify which component of anti-Ad immunity plays a role in potentializing anti-ovalbumin Ab responses, mice were injected with total splenocytes, purified $CD4^+$ or $CD8^+$ T cells or serum from Ad-immune mice and then challenged with AdF-3OVA2. Anti-ovalbumin humoral responses were boosted by anti-Ad serum or splenocytes but not by anti-Ad $CD4^+$ or $CD8^+$ T cells. From these results, we deduced that serum anti-Ad Abs were responsible for the enhanced anti-epitope humoral responses. In contrast, a role of anti-Ad cellular immunity was ruled out because anti-Ad $CD4^+$ or $CD8^+$ T cells did not modify anti-epitope humoral responses. Of note, the apparent contradiction with the boosting induced by total splenocytes could be resolved by the presence within splenocytes of plasma cells able to produce significant levels of anti-Ad Abs.

In sharp contrast to fiber-modified Ads, hexon-modified Ads reinjection led to a modest boost of anti-ovalbumin response. Moreover, anti-ovalbumin responses triggered by hexon-modified Ads were reduced in Ad-immune mice as compared to naive mice, thus suggesting that anti-Ad immune responses limit the efficiency of vaccination against the epitope embedded within hexon protein. This is in agreement with serum transfer experiments showing reduced anti-ovalbumin Ab levels in mice receiving anti-Ad serum before injection of hexon-modified Ads. Altogether, these results demonstrate that anti-Ad Abs impair the induction of antibody responses against an ovalbumin epitope inserted into hexon protein. As discussed by Getahun et al. for other antigens, two hypotheses, antigen clearance or epitope masking could explain Ab-mediated reduction of anti-epitope humoral responses (GETAHUN & HEYMAN, Scand J Immunol, 70, 277-87, 2009). The first hypothesis was invalidated since there was no difference in anti-Ad antibody induction and sensitivity between fiber and hexon-modified Ads. Thus, in contrast to previous data, deletion of hexon HVR5 does not modify significantly sensitivity to Ad Abs (ABE et al., J Gene Med, 11, 570-9, 2009). The second hypothesis, epitope masking by anti-Ad Abs, is strongly supported by the observation that epitope detection within hexon protein was inhibited in the presence of anti-Ad Abs. Such an influence of these Abs is not surprising given the fact that hexon protein is the major target of Ad neutralizing Abs (SUMIDA et al., J Immunol, 174, 7179-85, 2005; ROBERTS et al., Nature, 441, 239-43, 2006). Furthermore, since most of these Abs are directed against hexon HVRs, they may limit by steric hindrance epitope recognition by B cells.

It is also to be noted that following two administrations, anti-ovalbumin responses triggered by fiber-modified Ad were shown to be comparable to those induced by a recombinant Ad expressing ovalbumin as a transgene. This is noteworthy, given that the latter virus encodes the complete ovalbumin protein and not only 3OVA2 epitope.

The present study shades a new light on the determinants controlling the recently developed vaccination strategy based on epitope display by Ad. Indeed, we unravelled an unexpected role of anti-Ad Abs in controlling the vaccination efficacy against a capsid-embedded epitope. Depending on the site of epitope insertion, anti-Ad Abs were shown either to dramatically enhance (fiber insertion) or to reduce (hexon insertion) the humoral response against the epitope. A major novelty of our findings is to provide clues for choosing the best Ad-based vaccine to be used in clinic. Hence, one can anticipate that hexon-modified Ads should be more efficient for triggering anti-epitope responses in Ad-naïve patients. On the contrary, a better efficiency of Ad displaying epitope into fiber protein is expected in Ad5 seropositive patients or in case of repeated injections.

The invention claimed is:

1. A method of generating a humoral immune response against one or more target B-cell epitope(s) in a subject having a pre-existing humoral immunity against an adenovirus of a given serotype resulting from a previous exposure to a wild-type or recombinant adenovirus, comprising:
  administering to the subject a recombinant replication-defective adenovirus of the same serotype,
  wherein the subject has pre-existing humoral immunity to the same adenovirus serotype of said replication-defective adenovirus;
  said replication defective adenovirus has a heterologous polypeptide of up to 50 amino acids containing one or more target B-cell epitope(s) from a foreign antigen of interest inserted into the HI loop of the knob of a fiber protein of the replication-defective adenovirus, and an IgG humoral immune response against the target B-cell epitope(s) in the subject is enhanced by a pre-existing humoral immunity against said adenovirus serotype.

2. A method of generating a humoral immune response against one or more target B-cell epitope(s) in a subject comprising:
  (a) administering to the subject a recombinant replication-defective adenovirus having a heterologous polypeptide of up to 50 amino acids containing one or more target B-cell epitope(s) from a foreign antigen of interest inserted into the HI loop of the knob of a fiber protein of the recombinant replication deficient adenovirus, and
  (b) re-administering the recombinant replication-defective adenovirus at least once to the subject,
wherein IgG humoral immune response against the target B-cell epitope(s) is enhanced by humoral immunity generated against the recombinant replication-defective adenovirus.

3. The method of claim 1, wherein said recombinant replication-defective adenovirus further comprises one or more heterologous polypeptide(s) containing the same target B-cell epitope(s) inserted into a capsid protein other than the fiber protein.

4. The method of claim 1, further comprising re-administering at least once said recombinant replication-defective adenovirus to said subject.

5. The method of claim 3, further comprising re-administering at least once said recombinant replication-defective adenovirus to said subject.

6. The method of claim 1, wherein the subject is human.

7. The method of claim 2, wherein the subject is human.

8. The method of claim 3, wherein the subject is human.

9. The method of claim 4, wherein the subject is human.

10. The method of claim 5, wherein the subject is human.

* * * * *

SEQUENCE LISTING

```
<160> NUMBER OF SEQ ID NOS: 14

<210> SEQ ID NO 1
<211> LENGTH: 17
<212> TYPE: PRT
<213> ORGANISM: Artificial
<220> FEATURE:
<223> OTHER INFORMATION: Ovalbumin epitope

<400> SEQUENCE: 1

Ile Ser Gln Ala Val His Ala Ala His Ala Glu Ile Asn Glu Ala Gly
1               5                   10                  15

Arg

<210> SEQ ID NO 2
<211> LENGTH: 22
<212> TYPE: PRT
<213> ORGANISM: Artificial
<220> FEATURE:
<223> OTHER INFORMATION: Ovalbumin epitope

<400> SEQUENCE: 2

Ser Leu Lys Ile Ser Gln Ala Val His Ala Ala His Ala Glu Ile Asn
1               5                   10                  15

Glu Ala Gly Arg Glu Val
            20

<210> SEQ ID NO 3
<211> LENGTH: 13
<212> TYPE: PRT
<213> ORGANISM: Adenovirus

<400> SEQUENCE: 3

Thr Thr Glu Ala Ala Ala Gly Asn Gly Asp Asn Leu Thr
1               5                   10

<210> SEQ ID NO 4
<211> LENGTH: 10
<212> TYPE: PRT
<213> ORGANISM: Adenovirus

<400> SEQUENCE: 4

Thr Gln Glu Thr Gly Asp Thr Thr Pro Ser
1               5                   10
```

```
<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
atgggatgaa gctgctactg                                              20

<210> SEQ ID NO 6
<211> LENGTH: 65
<212> TYPE: DNA
<213> ORGANISM: Artificial
<220> FEATURE:
<223> OTHER INFORMATION: Primer

<400> SEQUENCE: 6
ggcatatctc aagctgtcca tgcagcacat gcagaaatca atgaagcagg cagacttggc  60
ggccc                                                              65

<210> SEQ ID NO 7
<211> LENGTH: 68
<212> TYPE: DNA
<213> ORGANISM: Artificial
<220> FEATURE:
<223> OTHER INFORMATION: Primer

<400> SEQUENCE: 7
ttagggccgc caagtctgcc tgcttcattg atttctgcat gtgctgcatg gacagcttga  60
gatatgcc                                                           68

<210> SEQ ID NO 8
<211> LENGTH: 80
<212> TYPE: DNA
<213> ORGANISM: Artificial
<220> FEATURE:
<223> OTHER INFORMATION: Primer

<400> SEQUENCE: 8
ggcagcctga agatatctca agctgtccat gcagcacatg cagaaatcaa tgaagcaggc  60
agagaggtgc ttggcggccc                                              80

<210> SEQ ID NO 9
<211> LENGTH: 83
<212> TYPE: DNA
<213> ORGANISM: Artificial
<220> FEATURE:
<223> OTHER INFORMATION: Primer

<400> SEQUENCE: 9
ttagggccgc caagcacctc tctgcctgct tcattgattt ctgcatgtgc tgcatggaca  60
gcttgagata tcttcaggct gcc                                          83

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
cagctccatc tcctaactgt agactaaatg                                   30
```

```
<210> SEQ ID NO 11
<211> LENGTH: 83
<212> TYPE: DNA
<213> ORGANISM: Artificial
<220> FEATURE:
<223> OTHER INFORMATION: Primer

<400> SEQUENCE: 11
gtaaccctaa ccattacact aaacggttct agcatatctc aagctgtcca tgcagcacat    60
gcagaaatca atgaagcagg agc                                           83

<210> SEQ ID NO 12
<211> LENGTH: 88
<212> TYPE: DNA
<213> ORGANISM: Artificial
<220> FEATURE:
<223> OTHER INFORMATION: Primer

<400> SEQUENCE: 12
gctagaacct ctgcctgctt cattgatttc tgcatgtgct gcatggacag cttgagatat    60
gctagaaccg tttagtgtaa tggttagg                                      88

<210> SEQ ID NO 13
<211> LENGTH: 108
<212> TYPE: DNA
<213> ORGANISM: Artificial
<220> FEATURE:
<223> OTHER INFORMATION: Primer

<400> SEQUENCE: 13
gtaaccctaa ccattacact aaacggttct agcagcctga agatatctca agctgtccat    60
gcagcacatg cagaaatcaa tgaagcaggc agagaggtgg gttctagc                108

<210> SEQ ID NO 14
<211> LENGTH: 103
<212> TYPE: DNA
<213> ORGANISM: Artificial
<220> FEATURE:
<223> OTHER INFORMATION: Primer

<400> SEQUENCE: 14
gctagaaccc acctctctgc ctgcttcatt gatttctgca tgtgctgcat ggacagcttg    60
agatatcttc aggctgctag aaccgtttag tgtaatggtt agg                     103
```